United States Patent
Gozlan et al.

(10) Patent No.: US 10,221,148 B2
(45) Date of Patent: Mar. 5, 2019

(54) COMPOSITIONS OF MONO-ALKYL ETHERS OF MONOANHYDRO-HEXITOLS, PRODUCTION METHODS THEREOF AND USE OF SAME

(71) Applicants: SYRAL BELGIUM NV, Aalst (BE); UNIVERSITÉ CLAUDE BERNARD LYON 1, Villeurbanne (FR); CENTRE NATIONAL DE LA RECHERCHE SCIENTIFIQUE (C.N.R.S.), Paris (FR)

(72) Inventors: Charlotte Gozlan, Villeurbanne (FR); Nicolas Duguet, Villeurbanne (FR); Marc Lemaire, Villeurbanne (FR); Andreas Redl, Aalst (BE)

(73) Assignees: SYRAL BELGIUM, Aalst (BE); UNIVERSITÉ CLAUDE BERNARD LYON 1, Villeurbanne (FR); CENTRE NATIONAL DE LA RECHERCHE SCIENTIFIQUE, Paris (FR)

(*) Notice: Subject to any disclaimer, the term of this patent is extended or adjusted under 35 U.S.C. 154(b) by 11 days.

(21) Appl. No.: 15/318,662

(22) PCT Filed: Jun. 11, 2015

(86) PCT No.: PCT/IB2015/054418
§ 371 (c)(1),
(2) Date: Dec. 13, 2016

(87) PCT Pub. No.: WO2015/189796
PCT Pub. Date: Dec. 17, 2015

(65) Prior Publication Data
US 2017/0121298 A1    May 4, 2017

(30) Foreign Application Priority Data
Jun. 13, 2014  (FR) .................................... 14 01346

(51) Int. Cl.
| | | |
|---|---|---|
| *C07C 43/10* | (2006.01) | |
| *C07H 15/04* | (2006.01) | |
| *C07H 3/10* | (2006.01) | |
| *C07D 307/20* | (2006.01) | |
| *B01F 17/00* | (2006.01) | |
| *C10M 129/20* | (2006.01) | |
| *C11D 1/66* | (2006.01) | |
| *A61K 8/49* | (2006.01) | |
| *A61Q 19/00* | (2006.01) | |

(52) U.S. Cl.
CPC .......... *C07D 307/20* (2013.01); *A61K 8/4973* (2013.01); *A61Q 19/00* (2013.01); *B01F 17/0021* (2013.01); *C07C 43/10* (2013.01); *C07H 3/10* (2013.01); *C07H 15/04* (2013.01); *C10M 129/20* (2013.01); *C11D 1/662* (2013.01); *C10M 2207/044* (2013.01)

(58) Field of Classification Search
CPC ........... C07C 43/10; C07H 15/04; C07H 3/10
See application file for complete search history.

(56) References Cited

FOREIGN PATENT DOCUMENTS

WO    WO2012/148530 A1    11/2012

OTHER PUBLICATIONS

International Search Report dated Jul. 28, 2015.

*Primary Examiner* — Theodore R. West
(74) *Attorney, Agent, or Firm* — Symbus Law Group, LLC; Clifford D. Hyra

(57) ABSTRACT

A composition of monoanhydro-hexitol monoalkyl ether isomers bearing an alkyl ether radical (OR) at C-3, C-5 or C-6 of the monoanhydro-hexitol, in which the alkyl group (R) is a linear or branched, cyclic or noncyclic hydrocarbon-based group comprising between 4 to 18 carbon atoms, the process for obtaining such a composition and the use thereof as a nonionic surfactant, emulsifier, lubricant, antimicrobial agent or dispersant.

18 Claims, 2 Drawing Sheets

COMPOSITIONS OF MONO-ALKYL ETHERS OF MONOANHYDRO-HEXITOLS, PRODUCTION METHODS THEREOF AND USE OF SAME

This application claims the benefit of French Patent Application No. 14/01346, filed Jun. 13, 2014, which is hereby incorporated by reference in its entirety.

FIELD OF THE INVENTION

The present invention relates to sugar-based monoalkyl ether compositions, and to a process for obtaining such ethers.

BACKGROUND

In the scientific and technical literature, sugar-based surfactant molecules are well known. Among them, fatty acid esters of sucrose, sorbitan esters and long-chain alkyl polyglucosides have been widely used in food, personal care and cosmetic or pharmaceutical applications. Some of these surfactants have also been widely used as domestic or industrial cleaning agents or as lubricants.

Despite their widespread use and acceptance, it is well known that ester-based surfactants are only stable over a limited pH range, while alkyl glucosides are stable under alkaline and neutral conditions, but not under strongly acidic conditions.

Other drawbacks are associated with the processes used for obtaining these derivatives. Specifically, in the case of long-chain higher alkyl glucosides, trans-glycosylation is necessary. The use of relatively complicated and expensive facilities is necessary in order to obtain a sufficiently pure product. In the case of sugar-based esters, especially sorbitan esters, expensive and toxic solvents are needed, or high reaction temperatures are then necessary to obtain the products in a sufficiently high yield.

In order to improve the stability under acidic conditions of sugar-based surfactant compounds, a sugar alcohol ether has recently been proposed in WO 2012/148530. This patent application describes a process for preparing polyol ethers in the course of which a mass of molten polyols is reacted with a long-chain alkyl aldehyde under reductive alkylation conditions and acid catalysis. According to this disclosure, difficult and extreme reaction conditions are required, in combination with high-pressure equipment in order to achieve the reductive alkylation reaction. In order to obtain the desired products, an excess of sugar alcohol is judged to be necessary relative to the aldehyde. This leads to large energy consumption per mole of sugar alcohol ether. In addition, at the end of each synthesis, the authors identified by $^{13}$C NMR the only compound synthesized (a single regioisomer with an alkyl chain in position 6), for example 2-(2-heptyloxy-1-hydroxy ethyl)tetrahydrofuran-3,4-diol (Example 1), 2-(2-hexyloxy-1-hydroxyethy)tetrahydrofuran-3,4-diol (Example 2) and 2-(2-octyloxy-1-hydroxy) ethyptetrahydrofuran-3,4-diol (Example 3).

Moreover, the prior art describes methods for obtaining monoanhydro-sorbitol. Thus, a method in which sorbitol is dissolved in water in the presence of an acid catalyst and heated under atmospheric conditions for a time sufficient to obtain the maximum content of 1,4-sorbitan is described in *Acta Chemical Scandinavica B* (1981) page 441-449. Similar processes were also disclosed in which the reaction is performed under reduced pressure (U.S. Pat. No. 2,390,395 and US 2007/173 651) or under moderate hydrogen pressure (US 2007/173 654). In patent application US 2007/173 654, a noble metal cocatalyst is used. However, the isosorbide concentrations measured are quite high, in comparison with the 1,4-sorbitan. Thus, the prior art methods do not make it possible to observe a high yield for the production of monoanhydro-sorbitol under mild reaction conditions.

SUMMARY

Thus, it is clear that there is a need to propose sugar alcohol ethers, with surfactant properties, which may be obtained via processes in high yield and which are environmentally acceptable, advantageous in terms of energy consumption and also industrially easy to perform.

This need was solved by establishing a composition of monoanhydro-hexitol monoalkyl ether isomers bearing an alkyl ether radical (OR) in position C-3, C-5 or C-6 of the monoanhydro-hexitol, in which the alkyl group (R) is a linear or branched hydrocarbon-based group comprising between 4 to 18 carbon atoms, preferentially between 8 and 12 carbon atoms.

The term "alkyl ether radical (OR) in position C-3, C-5 or C-6" means an alkoxy radical substituting a hydroxyl group (OH) borne by a carbon atom located in position 3, 5 or 6 of the monoanhydro-hexitol.

The expression "monoanhydro-hexitol monoalkyl ether isomers bearing an alkyl ether radical (OR) in position C-3, C-5 or C-6 of the monoanhydro-hexitol" or "isomers in position C-3, C-5 or C-6 of monoanhydro-hexitol monoalkyl ethers" means 3-alkyl monoanhydro-hexitol, 5-alkyl monoanhydro-hexitol and 6-alkyl monoanhydro-hexitol.

Examples of alkyl groups that may be mentioned include butyl, pentyl, hexyl, heptyl, octyl, nonyl, decyl, undecyl and dodecyl groups. Typically, the alkyl group is chosen from octyl, decyl and dodecyl groups.

More particularly, the composition according to the invention comprises at least 1%, 2%, 5%, 10% or 15% (w/w) of any one of the monoanhydro-hexitol monoalkyl ether isomers. Advantageously, the major isomer is 6-alkyl monoanhydro-hexitol. Typically, the 6-alkyl monoanhydro-hexitol isomer represents 34% to 98% (w/w) of the monoanhydro-hexitol monoalkyl ether isomers of the composition according to the invention, preferentially 40% to 80% (w/w), more preferentially 45% to 70% (w/w). 3-Alkyl monoanhydro-hexitol and 5-alkyl monoanhydro-hexitol may be in identical or different proportions and, independently of each other, may represent between 1% to 33% (w/w), preferentially 5% to 30% and more preferentially 10% to 27% (w/w) of the monoanhydro-hexitol monoalkyl ether isomers of the composition.

Preferentially, the ratio [(3-alkyl monoanhydro-hexitol+ 5-alkyl monoanhydro-hexitol)/6-alkyl monoanhydro-hexitol] is between 0.02 and 2, preferentially between 0.25 and 1.8, more preferentially between 0.4 and 1.7, between 0.7 and 1.5 or between 0.8 and 1.2.

Preferentially, the composition according to the invention comprises at least 90% (w/w), preferably at least 95% (w/w) of monoanhydro-hexitol monoalkyl ether isomers.

Advantageously, the monoanhydro-hexitol is chosen from monoanhydro-sorbitol, monoanhydro mannitol, monoanhydro iditol and monoanhydro galactitol. Typically, the monoanhydro-hexitol is monoanhydro sorbitol or monoanhydro mannitol.

Typically, the monoanhydro-sorbitol monoalkyl ether isomers may be of formula I in which R1, R2 and R3 are an alkyl group and two hydrogen atoms.

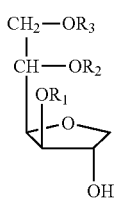

For example, a C-3 isomer of a monoanhydro-sorbitol alkyl ether (or 3-alkyl monoanhydro-sorbitol) is of formula II in which R1 is an alkyl group.

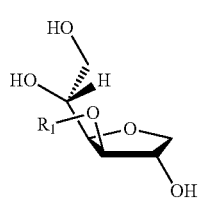

Preferentially, the C-5 isomer of a monoanhydro-sorbitol alkyl ether (or 5-alkyl monoanhydro-sorbitol) is of formula III in which R2 is an alkyl group.

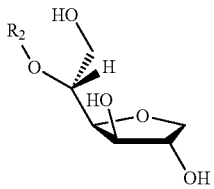

Preferentially, the C-6 isomer of a monoanhydro-sorbitol alkyl ether (or 6-alkyl monoanhydro-sorbitol) is of formula IV in which R3 is an alkyl group.

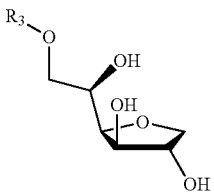

The present invention also relates to a process for obtaining a composition of monoanhydro-hexitol monoalkyl ether isomers bearing an alkyl ether radical (OR) in position C-3, C-5 or C-6 of the monoanhydro-hexitol, in which the alkyl group (R) comprises 4 to 18 carbon atoms according to the invention, said process comprising the following steps:

dehydration of a hexitol to obtain a monoanhydro-hexitol substrate;

production of a hexitan alkyl acetal by acetalization or trans-acetalization of the monoanhydro-hexitol substrate obtained, with an aliphatic aldehyde reagent comprising from 4 to 18 carbon atoms, by acetalization, preferentially in a substrate/reagent ratio of between 5/1 and 1/1, or a derivative of an aliphatic aldehyde reagent comprising from 4 to 18 carbon atoms, by trans-acetalization, preferentially, in a substrate/reagent ratio of between 1/1 and 1/3, catalytic hydrogenolysis of the hexitan alkyl acetal, and recovery of a composition of monoanhydro-hexitol monoalkyl ether isomers bearing an alkyl ether radical (OR) in position C-3, C-5 or C-6 of the monoanhydro-hexitol, in which the alkyl group (R) comprises 4 to 18 carbon atoms.

Typically, the process according to the invention also comprises at least one step of neutralization, and/or of filtration and/of of purification after any of the steps a), b) and/or d).

Preferentially, the dehydration step a) is performed by treating hexitol, for example in the form of a molten mass of hexitol, with an acid catalyst.

Typically, step a) is performed under a hydrogen atmosphere preferentially at a pressure of 20 to 50 bar.

Advantageously, step a) is performed at a temperature of between 120 and 170° C., preferentially between 130 and 140° C.

The acetalization or trans-acetalization step b) may be preceded by a step of purification of the monoanhydro-hexitol. The purification may be, for example, a chromatography or crystallization step.

Preferentially, the acetalization or trans-acetalization step b) comprises:

bi) optionally, a first step of preheating the monoanhydro-hexitol substrate, preferentially, to a temperature of between 70 and 130° C., typically between 90 and 110° C.;

bii) a step of adding the aliphatic aldehyde reagent or the aliphatic aldehyde derivative and biii) a step of adding a catalyst, preferentially an acid catalyst.

Typically, the acetalization or trans-acetalization reaction is performed at temperatures of between 70 and 130° C., typically between 75 and 110° C., typically 77 and 110° C. The reaction mixtures are heated to temperatures varying as a function of the reagents and solvents used. Typically, for a C5 or C12 aliphatic aldehyde reagent or aliphatic aldehyde derivative, when the solvent is ethanol, the acetalization or trans-acetalization temperature may be 80° C.; when the acetalization or trans-acetalization is performed in the absence of solvent, the reaction temperature may be 95° C. The reaction time is determined by the degree of conversion reached.

The acid catalysts used in steps a) and b) may be chosen independently from solid or liquid, organic or inorganic acids, solid acids being preferred. In particular, the preferred acids are chosen from para-toluenesulfonic acid, methanesulfonic acid and camphorsulfonic acid (CSA) and sulfonic resins.

During the execution of the acetalization or trans-acetalization reaction with an aliphatic aldehyde reagent or an aliphatic aldehyde derivative, the reaction may be performed with or without solvent. When the reaction is performed in the presence of a solvent, the solvent is preferentially a polar solvent, typically a nonaqueous polar solvent.

During the use of a solvent, it may be chosen from polar aprotic solvents such as dimethylformamide (DMF), dimethyl sulfoxide (DMSO), dimethylacetamide (DMA), acetonitrile (CH$_3$CN), tetrahydrofuran (THF), 2-methyltetrahydrofuran (2Me-THF), cyclopentyl methyl ether (CPME), dibutyl ether (DBE), methyl tert-butyl ether (MTBE) or trimethoxypropane (TMP) or polar protic solvents such as methanol (MeOH), ethanol (EtOH), butanol (BuOH) or isopropanol. Polar protic solvents such as ethanol are particularly advantageous.

The acetalization step b) may be performed with an aliphatic aldehyde reagent, in which the aldehyde reagent contains from 4 to 18 carbon atoms. These aldehydes may be chosen from linear or branched aliphatic aldehydes. In a preferred embodiment, the aliphatic aldehydes contain from 4 to 18 carbon atoms, preferentially 5 to 12 carbon atoms. Certain typical representatives of the aldehydes are: pentanal, hexanal, heptanal, octanal, nonanal, decanal, undecanal and dodecanal.

Extensive experimental studies have made it possible to select conditions that ensure optimum degrees of conversion and yields for the acetalization step b). The best results were obtained when the mole ratio of the substrate to the reagent is between 5/1 and 1/1, preferably between 4/1 and 1/1 and more preferably between 3/1 and 2/1.

The trans-acetalization step b) may be performed in the presence or absence of a solvent so as to obtain sugar-based, long-chain alkyl cyclic acetals.

Typically, when the trans-acetalization step b) is performed in the presence of a solvent, the preferred solvent is the alcohol corresponding to the acetal reagent used.

In the course of the trans-acetalization step b), the derivatives of an aliphatic aldehyde reagent may be the dialkyl acetals of the corresponding aldehydes. The dimethyl acetals and diethyl acetals are preferred.

Extensive experimental studies have made it possible to select conditions which ensure that, during the trans-acetalization reactions, optimum yields and degrees of conversion were obtained when the mole ratio of the substrate to the reagent is between 1/1 and 1/3, and preferably between 2/3 and 2/5. The catalysts used are the same as during the acetalization reactions.

Typically, step c) of hydrogenolysis of the hexitan alkyl acetal may be preceded by a filtration and/or purification step.

The purification may be, for example, a chromatography or crystallization step. Preferentially, purification by chromatography is performed using a nonaqueous polar solvent. For example, the nonaqueous polar solvent is identical to the one used in the hydrogenolysis step c).

Advantageously, the hydrogenolysis step c) is performed at a temperature of between 80° C. and 140° C., preferentially at a pressure of between 15 and 40 bar.

The hydrogenolysis step c) may be performed with or without solvent. When it is performed in the presence of solvents, the solvents may be apolar, for instance heptane or dodecane. However, polar solvents and more particularly nonaqueous aprotic solvents are preferred since, for an equivalent selectivity, they allow better conversion than apolar solvents. Examples of aprotic solvents are, inter alia, without being limiting, trimethoxypropane (TMP), methyl tert-butyl ether (MTBE), THF, 2Me-THF, dibutyl ether (DBE) and cyclopentyl methyl ether (CPME). Preferentially, the aprotic solvent is CPME.

The hydrogenolysis step c) is preferentially performed in a polar aprotic solvent, at a temperature between 80° C. and 140° C. and a pressure between 15 and 40 bar, in the presence of a catalyst suitable for performing hydrogenolysis reactions.

Preferably, the hydrogenolysis step c) is performed in a nonaqueous polar solvent, at a temperature of between 100° C. and 130° C. and/or at a pressure of between 25 and 35 bar.

Typically, step c) is performed in the presence of a suitable catalyst such as a catalyst based on precious metals, or based on metals belonging to the ferrous metals group.

As a guide, a catalyst based on metals belonging to the ferrous metals group may be nickel, cobalt or iron.

Preferably, the hydrogenolysis is performed using a catalyst based on precious metals, such as palladium, rhodium, ruthenium, platinum or iridium.

Typically, the catalyst used in step c) may be attached to a support such as charcoal, alumina or silica. Such a support is, for example, in the form of beads. A catalyst based on palladium attached to charcoal beads (Pd/C) is preferred.

According to the invention, the hexitol such as the one used in step a) is a hydrogenated monosaccharide preferentially chosen from sorbitol, mannitol, iditol and galactitol, and a mixture thereof. Sorbitol and/or mannitol are preferred.

When the hexitol is sorbitol, the monoanhydro-hexitol obtained is 1,4-sorbitan of formula (V).

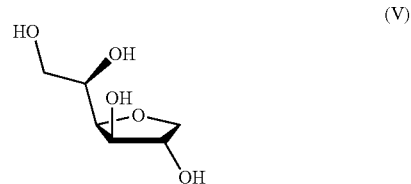

(V)

The inventors have demonstrated that the intermediate product 1,4-sorbitan could be obtained in good yield by treating a molten mass of sorbitol with a solid acid catalyst under a hydrogen atmosphere at a pressure of 20 to 50 bar, at a reaction temperature which may range between 120 and 170° C., for a sufficient period of time so as to obtain an optimum yield of sorbitan. The preferred reaction temperatures are between 130 and 140° C.

The reaction mixture thus obtained is formed from 1,4-sorbitan, unreacted sorbitol, isosorbide and minor amounts of byproducts, as illustrated in the chromatogram represented in FIG. 1. One of the advantages thus observed is the reduction in the level of coloring, in contrast with the standard prior processes.

The dehydration step a) may optionally be followed by a step of purifying the 1,4-sorbitan. Thus, the 1,4-sorbitan is purified from the reaction mixture and the remainder is recycled into the dehydration step. In a particular embodiment, the 1,4-sorbitan is recovered and purified by crystallization. In another preferred embodiment, the 1,4-sorbitan is recovered and purified by chromatography. This purified 1,4-sorbitan is preferably used as substrate for the acetalization reaction.

When the acetalization step b) is performed without solvent, the 1,4-sorbitan is first heated to between 90 and 110° C., and the aldehyde reagent is then added slowly, followed by addition of the catalyst.

The sorbitan acetal compositions obtained via the processes described above are composed of 4 isomers. This is illustrated in FIG. 2. Two of these isomers correspond to a diastereomeric mixture of 5-membered sorbitan acetal in position 5, 6 and the other two isomers correspond to a diastereomeric mixture of 6-membered sorbitan acetal in position 3, 5.

The sorbitan acetals in position 5, 6 are of formula VI in which the group R' is an alkyl group. Typically, R' is a linear or branched C3 to C17 aliphatic chain.

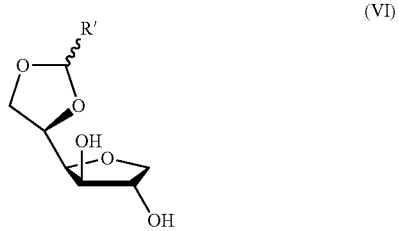

(VI)

The sorbitan acetals in position 3, 5 are of formula VII in which the group R is an alkyl group. Typically, R' is a linear or branched C3 to C17 aliphatic chain.

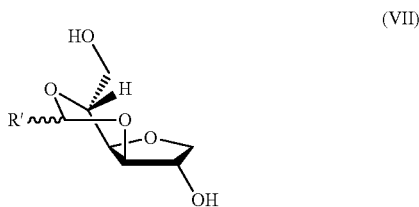

(VII)

The hexitan alkyl acetals obtained above are then subjected to a hydrogenolysis reaction. This acetal mixture may be used after recovery of the crude mixture, or alternatively after chromatographic purification. This hydrogenolysis reaction is performed in a polar aprotic solvent, at a temperature of between 80° C. and 140° C. and a pressure of between 15 and 40 bar, in the presence of a catalyst that is suitable for performing hydrogenolysis reactions.

Preferably, the hydrogenolysis is performed in a nonaqueous polar solvent, at a temperature of between 100° C. and 130° C. and a pressure of between 25 and 35 bar.

The nonaqueous polar solvent CPME (cyclopentyl methyl ether) proved to be particularly advantageous in the hydrogenolysis reaction of the 5, 6 and 3, 5 cyclic acetals of sorbitan.

The invention also relates to the product obtained by performing the process.

The invention furthermore relates to the use of the composition according to the invention as a nonionic surfactant, emulsifier, lubricant, antimicrobial agent or dispersant. Typically, the composition according to the invention may be used in a food or non-food product or in a pharmaceutical or cosmetic product.

When the composition according to the invention is used as a nonionic surfactant, dispersant or emulsifier, the food product may be chosen from aerated products such as mousses, ice cream, or non-aerated products such as spreading fats or vinaigrettes. The food product may be in the form of a liquid product chosen from the group formed by sauces, soups and drinks.

Preferentially, C10-C12 alkyl groups are preferred for their use as antimicrobial agent or nonionic surfactant.

Preferentially, C5-C8 alkyl groups are preferred in the use as emulsifier, lubricant or dispersant.

Without limiting the scope of the invention, the invention will now be illustrated further with the aid of a certain number of examples describing the methods for preparing these derivatives.

BRIEF DESCRIPTION OF THE DRAWINGS

Figures

DETAILED DESCRIPTION OF EMBODIMENTS OF THE INVENTION

Examples

Example 1

Figure 1:
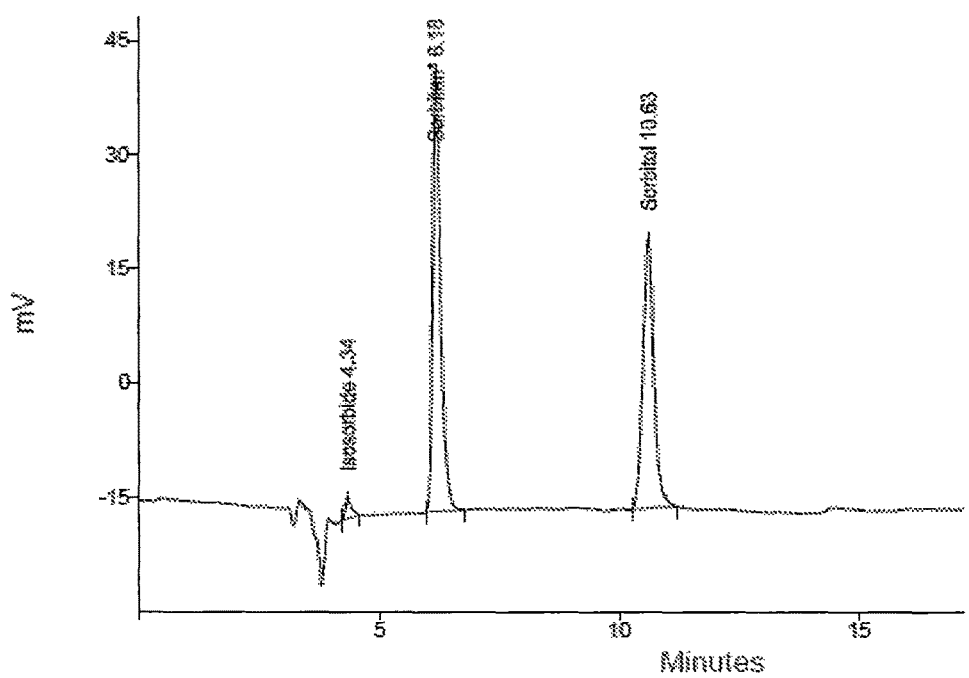
FIG. 1: represents a chromatogram of the reaction mixture obtained in the course of the dehydration reaction according to Example 1.

Dehydration of Sorbitol:

D-sorbitol (20 g, 110 mmol) and 0.1 mol % of camphorsulfonic acid are added to a 150 mL stainless-steel autoclave. The reactor is hermetically closed, purged three times with hydrogen and hydrogen was then introduced up to a pressure of 50 bar. The system is then heated at 140° C. and stirred with a mechanical stirrer for 15 hours. After cooling to room temperature, the hydrogen pressure was released and the white foam was diluted in ethanol (200 mL) to obtain a homogeneous yellow mixture. The solvent is evaporated off under reduced pressure and the residue is then crystallized from cold methanol and filtered under vacuum. The crystalline material was washed with cold methanol to give 1,4-sorbitan (5.88 g, 35% of theoretical) in the form of a white solid. The purity is >98%, as determined by HPLC, while the crystals showed a melting point of 113-114° C. The degree of conversion of the reaction was determined as 73%, by means of which a mixture of sorbitol, 1,4-sorbitan, isosorbide and a few byproducts in vary limited amount is obtained, such that the 1,4-sorbitan/isosorbide ratio was determined as being 80/20.

Example 2

Acetalization of sorbitan in DMF:

1,4-Sorbitan (X) (0.5 g, 3 mmol) was dissolved in DMF (1.4 mL) in a sealed tube. Valeraldehyde (Y) (107 µL, 1 mmol) was added dropwise under argon, followed by addition of camphorsulfonic acid (10 mg, 10% w/w), followed by closing the tube. The mixture is heated to 95° C. with magnetic stirring. After 15 hours, the dark reaction mixture was cooled and the solvent evaporated off under reduced pressure. A degree of conversion of 95% was reached. The residue was diluted in ethyl acetate and the excess 1,4-sorbitan was filtered off and washed with ethyl acetate. The filtrate was concentrated under reduced pressure. The residue is purified by flash chromatography (EtOAc/cyclohexane 80/20 to 100/0) to give sorbitan acetal (0.22 g, 89% isolated yield) in the form of a colorless oil. HPLC revealed a mixture of 4 isomers.

Example 3

In this example, various ratios of sorbitan against the aldehyde reagent were tested. The same reaction conditions as in Example 2 were used, but the sorbitan/aldehyde ratio ranged between 1/1 and 3/1. The results are presented in Table 1 below.

TABLE 1

Effect of the sorbitan/aldehyde ratio on the degree of conversion and the isolated yield

| Ratio X/Y | Conversion | Isolated yield (weight %) |
|---|---|---|
| 1/1 | 96% | 62% |
| 2/1 | 81% | 83% |
| 3/1 | 95% | 89% |

The above results show that excess sugar is advantageous in that it can prevent the formation of byproducts such as sugar diacetals. The unreacted sugar may be recovered at the end of the reaction.

Example 4

With a sorbitan/aldehyde ratio of 3/1, various aldehyde reagents were used to give sorbitan acetal reaction products. The same reaction conditions and the same purification steps as in Example 2 were used.
The results are presented in Table 2.

TABLE 2

| Aldehyde | Conversion | Isolated yield |
|---|---|---|
| Hexanal | 100% | 98% |
| Octanal | 89% | 95% |
| Decanal | 69% | 85% |
| Dodecanal | 61% | 80% |

Example 5

Besides the use of DMF as solvent, other solvents were also used to prepare the sorbitan acetal compositions. In this case also, the same reagents were used and the same procedure was followed as in Example 2, except that the reaction temperatures were about 80° C. The results are presented in Table 3.

TABLE 3

| Solvent | Conversion | Isolated yield |
|---|---|---|
| Acetonitrile | 100% | 75% |
| i-PrOH | 97% | 66% |
| DMF | 92% | 92% |

Example 6

Sorbitan acetalization without solvent:
1,4-Sorbitan (X) (0.5 g, 3 mmol) was heated to 95° C. in a sealed tube. Valeraldehyde (Y) (107 µL, 1 mmol) was added dropwise, under argon, followed by camphorsulfonic acid (10 mg, 10% w/w), before closing the tube. The mixture is heated to 95° C. with magnetic stirring. After 15 hours, the dark reaction mixture was cooled and diluted in ethyl acetate (2 mL) and the solvent is then evaporated off under reduced pressure. A degree of conversion of 80% was obtained. The residue was again diluted in ethyl acetate and the excess 1,4-sorbitan was filtered off and washed with ethyl acetate. The filtrate was concentrated under reduced pressure. The residue is purified by flash chromatography (EtOAc/cyclohexane 80/20 to 100/0) to give the sorbitan acetal (0.13 g, 54% isolated yield) in the form of a colorless oil. HPLC revealed a mixture of 4 isomers.

Example 7

Trans-acetalization of sorbitan in ethanol:
1,4-Sorbitan (0.5 g, 3 mmol) was dissolved in ethanol (7.5 mL) in a round-bottomed flask and 1,1-diethoxypentane (1.15 mL, 6 mmol) was added under a stream of argon, followed by camphorsulfonic acid (50 mg; 10% w/w). The mixture is heated to 80° C. with magnetic stirring. After 3 hours, the mixture was neutralized and concentrated under reduced pressure. The residue was purified by flash chromatography (ethyl acetate/cyclohexane 80/20 to 100/0) to give the sorbitan acetal (0.43 g, 66% isolated yield) in the form of a colorless oil. HPLC revealed a mixture of 4 isomers.

Example 8

Figure 2:
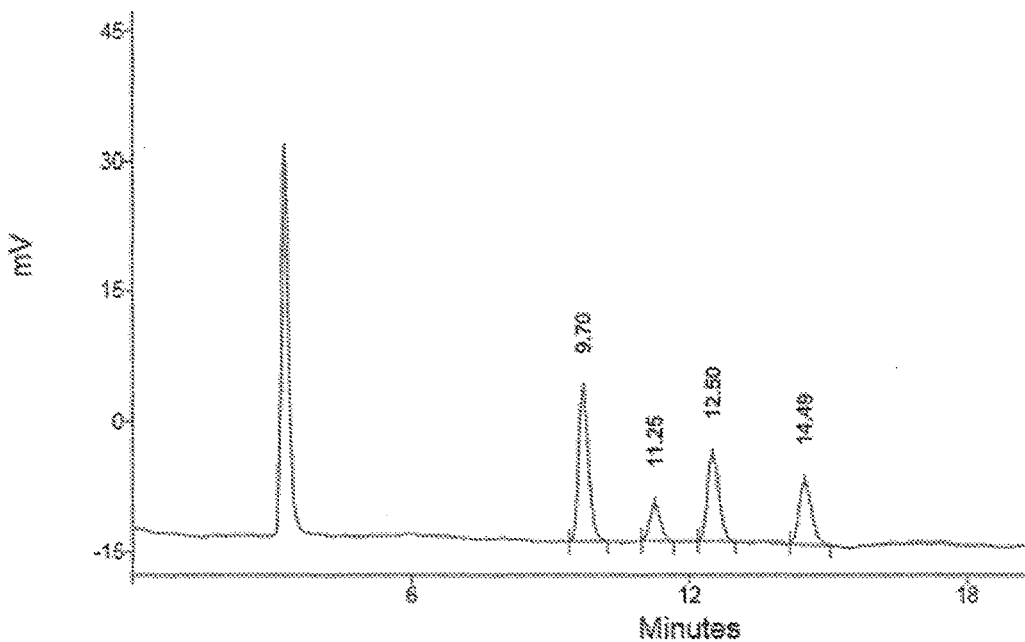
FIG. 2: represents a chromatogram of the reaction mixture obtained by trans-acetalization without solvent according to Example 8.

Trans-acetalization of sorbitan without solvent:

1,4-Sorbitan (0.5 g, 3 mmol) and 1,1-diethoxypentane (1,1-DEP) (1.15 mL, 6 mmol) (mole ratio 1/2) were placed in a round-bottomed flask under a stream of argon, followed by camphorsulfonic acid (50 mg; 10 w/w %). The mixture is heated to 80° C. with magnetic stirring. After 3 hours, the mixture was purified directly by flash chromatography (ethyl acetate/cyclohexane 80/20 to 100/0) to give the sorbitan acetal (0.517 g, 73% isolated yield) in the form of a colorless oil. HPLC revealed a mixture of 4 isomers. (FIG. 2)

Example 9

The trans-acetalization reactions without solvent were performed using various mole ratios, various reagents (1,1-dimethoxypentane), various reaction temperatures and various reaction times, the catalyst being the same. Purification of the reaction mixtures was performed by flash chromatography, as in Example 8.
The results are given in Table 4.

TABLE 4

| Reagent | Sorbitan/ reagent ratio | Time (h) | Temperature yield | Conversion | Isolated yield |
|---|---|---|---|---|---|
| 1,1-DMP | 1/1 | 15 | 70° C. | 99% | 66% |
| 1,1-DEP | 1/1 | 15 | 70° C. | 81% | 66% |
| 1,1-DEP | 1/1 | 15 | 80° C. | — | 49% |
| 1,1-DEP | 1/2 | 3 | 80° C. | 80% | 73% |

The trans-acetalization reactions starting with 1,1-DMP or 1,1-DEP are particularly pertinent in the reaction without solvent in which sorbitan and 1,1-DEP are in stoichiometric proportions.

Example 10

Figure 3:
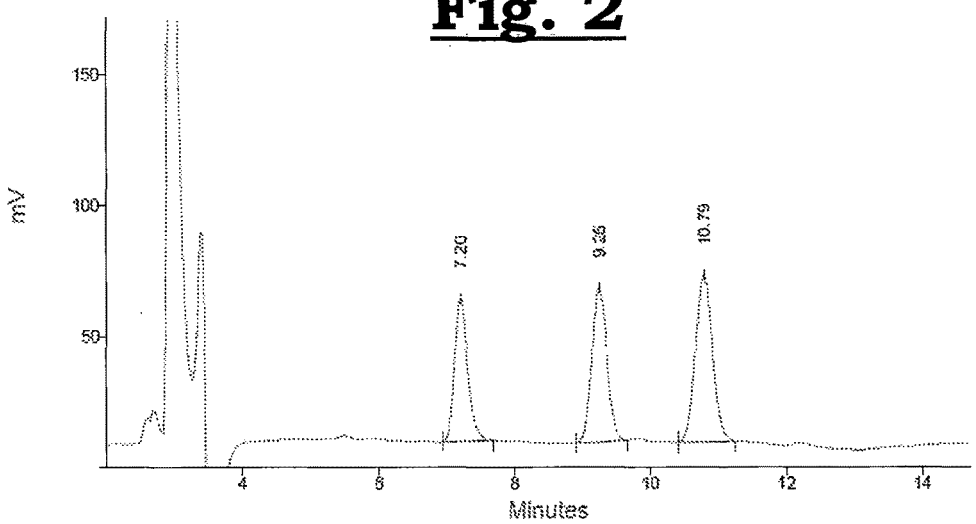
FIG. 3: represents a chromatogram of the reaction mixture obtained by hydrogenolysis according to Example 10.

Hydrogenolysis of sorbitan acetals:
Pentylidene-(1,4)-sorbitan (51/49 mixture of regioisomers, 0.98 g, 4.22 mmol) was diluted in dry CPME (30 mL) and placed in a stainless-steel autoclave, with 5% Pd/C catalyst (0.45 g). The reactor is firmly closed and purged three times with hydrogen, and hydrogen is then introduced under pressure (30 bar). The system is heated at 120° C. and stirred for 15 hours. After cooling to room temperature, the hydrogen under pressure is released, the reaction mixture is dissolved in absolute ethanol (100 mL) and filtered (0.01 micron Millipore Durapore filter). The filtrate is evaporated under reduced pressure and the residue is purified by flash chromatography (EtOAc/cyclohexane 90/10 to 100/0, then EtOH/EtOAc 10/90). A mixture of (1,4)-sorbitan pentyl ethers (0.686 g, 69%) was thus obtained in the form of a colorless oil. Analysis by HPLC (C18 column, water/$CH_3CN$ 80/20+0.1% v/v $H_3PO_4$ eluent) showed a 27/33/40 mixture of pentyl(1,4)sorbitan regioisomers in positions 5, 3 and 6. The retention times $R_t$ are 7.20 min (27%), 9.25 min (33%) and 10.79 min (40%) (the peaks having been assigned, respectively, to the regioisomers in positions 5, 3 and 6) (FIG. 3). Spectroscopic data: $^1H$ NMR (400 MHz, $d_6$-DMSO) $\delta_H$ 0.85 (3H, t, J=7), 1.20-1.37 (4H, m), 1.38-1.58 (2H, m), 3.20-3.98 (10H, m, sorbitan protons+$OCH_2$ ethers), 4.02-5.15 (3H, 7 m, OH protons); $^{13}C$ NMR (100 MHz, $d_6$-DMSO) Sc for major isomer: 13.99 ($CH_3$), 22.01 ($CH_2$), 27.88 ($CH_2$), 28.99 ($CH_2$), 67.50 (CH), 70.59 ($CH_2$), 73.36 ($CH_2$), 73.49 ($CH_2$), 75.66 (CH), 76.37 (CH), 80.34 (CH). $\delta_C$ for minor isomers: 14.02 (2 $CH_3$), 22.03 (2 $CH_2$), 27.86 and 27.91 (2 $CH_2$), 29.21 and 29.55 (2 $CH_2$), 62.02 ($CH_2$), 64.20 ($CH_2$), 68.71 (CH), 69.51 ($CH_2$), 69.79 ($CH_2$), 73.15 ($CH_2$), 73.23 (CH), 73.60 ($CH_2$), 75.53 (CH), 76.45 (CH), 77.37 (CH), 79.28 (CH), 80.10 (CH), 83.95 (CH). HRMS (ESI$^+$) calculated for $C_{11}H_{22}NaO_5$: 257.1363 [M+Na]$^+$; found: 257.1359 (−1.4 ppm).

Example 11

"One-pot" synthesis of sorbitan ethers from 1,4-sorbitan:
  1,4-Sorbitan (10 g, 62 mmol) is dissolved in dry CPME (30 mL) in a 100 mL round-bottomed flask in the presence of $Na_2SO_4$ (6.5 g, 50 mmol), under an argon atmosphere. Valeraldehyde (3.3 mL, 31 mmol) is added dropwise, followed by Amberlyst 15 (530 mg, 20 w/w % of valeraldehyde). The mixture is heated to 80° C. with magnetic stirring. After 3 hours, the hot mixture is filtered, washed with CPME (2×25 mL) and the filtrate is concentrated under reduced pressure. Without additional purification, the mixture is diluted in CPME (300 mL), dried over $MgSO_4$ and filtered. The filtrate is introduced into a 500 mL stainless-steel autoclave, and 5%-Pd/C (3.3 mg) is added. The reactor is firmly closed and purged three times with hydrogen, and hydrogen is then introduced under pressure (30 bar). The system is heated at 120° C. and stirred for 15 hours. After cooling to room temperature, the hydrogen under pressure is released, the reaction mixture is dissolved in absolute ethanol (250 mL) and filtered (0.01 micron Millipore Durapore filter). The filtrate is evaporated under reduced pressure and the residue (5.8 g) is purified by flash chromatography (EtOAc/cyclohexane 90/10 to 100/0, and then EtOH/EtOAc 10/90). A mixture of (1,4)sorbitan pentyl ethers (3.97 g, 56%) was obtained in the form of a colorless oil (purity >98% by $^1H$ NMR).

Example 12

Octyl-1,4-sorbitan is prepared according to the procedure described in Example 10, starting with octylidene-1,4-sorbitan (39/61 mixture of regioisomers) (5.61 g, 20.4 mmol). The residue is purified by flash chromatography (EtOAc/cyclohexane 80/20 to 100/0 and then EtOH/EtOAc 10/90) to give a mixture of octyl-1,4-sorbitan isomers as a solid white product. Analysis by HPLC (C18 column, water/$CH_3CN$ 80/20+0.1% v/v $H_3PO_4$ eluent) showed a 33/22/45 mixture of regioisomers of octyl(1,4)-sorbitan in positions 5, 3 and 6 (the peaks having been assigned, respectively, to the regioisomers in positions 5, 3 and 6).
  Spectroscopic data: $^1H$ NMR (300 MHz, $d_6$-DMSO) $\delta_H$ 0.86 (3H, t, J=7), 1.08-1.39 (10H, m), 1.39-1.58 (2H, m), 3.28-3.95 (10H, m, sorbitan protons+$OCH_2$ ethers), 4.02-5.10 (3H, 7m, OH protons); $^{13}C$ NMR (75 MHz, $d_6$-DMSO): $\delta_C$ for major isomer: 13.98 ($CH_3$), 22.12 ($CH_2$), 25.69 ($CH_2$), 28.73 ($CH_2$), 28.92 ($CH_2$), 29.31 ($CH_2$), 31.29 ($CH_2$), 67.48 (CH), 70.60 ($CH_2$), 73.35 ($CH_2$), 73.48 ($CH_2$), 75.64 (CH), 76.36 (CH), 80.33 (CH) $\delta_C$ for minor isomers: 13.98 (2 $CH_3$), 22.12 (2 $CH_2$), 25.69 (2 $CH_2$), 28.88 (2 $CH_2$), 28.92 (2 $CH_2$), 28.98 ($CH_2$), 29.52 ($CH_2$), 29.88 ($CH_2$), 31.32 ($CH_2$), 62.00 ($CH_2$), 64.17 ($CH_2$), 68.69 (CH), 69.51 ($CH_2$), 69.82 ($CH_2$), 73.14 ($CH_2$), 73.22 (CH), 73.59 ($CH_2$), 75.53 (CH), 76.44 (CH), 77.37 (CH), 79.27 (CH), 80.07 (CH), 83.94 (CH) HRMS (ESI$^+$) calculated for $C_{14}H_{28}NaO_5$: 299.1829 [M+Na]$^+$; found: 299.1832 (−1.2 ppm)

Example 13

Decyl-1,4-sorbitan is prepared according to the procedure described in Example 10, starting with decylidene-1,4-sorbitan (36/64 mixture of regioisomers) (6.12 g, 20.2 mmol). The residue is purified by flash chromatography (EtOAc/cyclohexane 70/30 to 100/0 and then EtOH/EtOAc 10/90) to give a mixture of decyl-1,4-sorbitan isomers as a solid white product. Analysis by HPLC (C18 column, water/$CH_3CN$ 50/50+0.1% v/v $H_3PO_4$ eluent) showed a 32/16/52 mixture of regioisomers of decyl-(1,4)-sorbitan in positions 5, 3 and 6 (the peaks having been assigned, respectively, to the regioisomers in positions 5, 3 and 6).
  Spectroscopic data: $^1H$ NMR (300 MHz, $d_6$-DMSO) $\delta_H$ 0.86 (3H, t, J=7), 1.09-1.38 (14H, m), 1.38-1.58 (2H, m), 3.25-4.01 (10H, m, sorbitan protons+$OCH_2$ ethers), 4.02-5.08 (3H, 7 m, OH protons); $^{13}C$ NMR (75 MHz, $d_6$-DMSO) $\delta_C$ for major isomer: 13.98 ($CH_3$), 22.16 ($CH_2$), 25.76 ($CH_2$), 28.79 ($CH_2$), 29.04 ($CH_2$), 29.07 ($CH_2$), 29.14 ($CH_2$), 29.17 ($CH_2$), 29.35 ($CH_2$), 67.53 (CH), 70.63 ($CH_2$), 73.38 ($CH_2$), 73.50 ($CH_2$), 75.69 (CH), 76.40 (CH), 80.35 (CH). $\delta_C$ for minor isomers: 13.98 (2 $CH_3$), 22.16 (2 $CH_2$), 28.98 (2 $CH_2$), 29.01 (2 $CH_2$), 29.14 (2 $CH_2$), 29.17 (2 $CH_2$), 29.35 (2 $CH_2$), 29.57 (2 $CH_2$), 29.92 (2 $CH_2$), 62.01 ($CH_2$), 64.18 ($CH_2$), 68.72 (CH), 69.56 ($CH_2$), 69.84 ($CH_2$), 73.16 ($CH_2$), 73.27 (CH), 73.60 ($CH_2$), 75.56 (CH), 76.48 (CH), 77.41 (CH), 79.30 (CH), 80.08 (CH), 83.96 (CH) HRMS (ESI$^+$) calculated for $C_{16}H_{32}NaO_5$: 327.2142 [M+Na]$^+$; found: 327.2135 (+2.1 ppm).

The invention claimed is:
  1. A composition of monoanhydro-hexitol monoalkyl ether isomers bearing an alkyl ether radical (OR) in position C-3, C-5 or C-6 of the monoanhydro-hexitol, in which the alkyl group (R) is a linear or branched hydrocarbon-based group comprising between 4 to 18 carbon atoms.
  2. The composition as claimed in claim 1, wherein the monoanhydro hexitol is chosen from monoanhydro sorbitol, monoanhydro mannitol, monoanhydro iditol and monoanhydro galactitol and mixtures thereof.
  3. The composition as claimed in claim 1, comprising at least 1% (w/w) of any one monoanhydro-hexitol monoalkyl ether isomers.
  4. The composition as claimed in claim 1, comprising at least 90% (w/w) of monoanhydro-hexitol monoalkyl ether isomers.

5. The composition as claimed in claim 1, wherein a ratio of [(3-alkyl monoanhydro-hexitol+5-alkyl monoanhydro-hexitol) to 6-alkyl monoanhydro-hexitol] is between 0.02 and 2.

6. The composition as claimed in claim 1, wherein the alkyl group (R) comprises between 8 and 12 carbon atoms.

7. A process for obtaining a composition of monoanhydro-hexitol monoalkyl ether isomers bearing an alkyl ether radical (OR) in position C-3, C-5 or C-6 of the monoanhydro-hexitol, in which the alkyl group (R) comprises between 4 to 18 carbon atoms, comprising the following steps:
   a) dehydration of a hexitol to obtain a monoanhydro-hexitol substrate;
   b) production of a hexitan alkyl acetal by acetalization or trans-acetalization of the monoanhydro-hexitol substrate obtained, with
      i. an aliphatic aldehyde reagent comprising from 4 to 18 carbon atoms, by acetalization, or
      ii. a derivative of an aliphatic aldehyde reagent comprising from 4 to 18 carbon atoms, by trans-acetalization,
   c) catalytic hydrogenolysis of the hexitan alkyl acetal without acid catalyst, and
   d) recovery of a composition of monoanhydro-hexitol monoalkyl ether isomers bearing an alkyl ether radical (OR) in position C-3, C-5 or C-6 of the monoanhydro-hexitol, in which the alkyl group (R) comprises 4 to 18 carbon atoms according to claim 1.

8. The process as claimed in claim 7, wherein the acetalization or trans-acetalization step b) is performed in the presence of an acid catalyst.

9. The process as claimed in claim 7, wherein the hydrogenolysis is performed in a solvent or without solvent, in the presence of a catalyst.

10. The process as claimed in claim 9, wherein the solvent is a polar solvent.

11. The process as claimed in claim 9, wherein the hydrogenolysis is performed at a temperature of between 80 and 140° C. and/or a pressure of between 15 and 40 bar.

12. The process as claimed in claim 9, wherein the hydrogenolysis is performed in the presence of a catalyst based on precious metals.

13. The process as claimed in claim 7, further comprising at least one filtration and/or purification step after any one of steps a), b) and/or d).

14. The process as claimed in claim 13, wherein the purification step is performed by chromatography or crystallization.

15. The process as claimed in claim 7, wherein the hexitol is chosen from sorbitol and mannitol.

16. The process as claimed in claim 7, wherein the aliphatic aldehyde reagent comprising from 4 to 18 carbon atoms is acetalized in a substrate/reagent ratio of between 5/1 and 1/1.

17. The process as claimed in claim 7, wherein the derivative of an aliphatic aldehyde reagent comprising from 4 to 18 carbon atoms is trans-acetalized in a substrate/reagent ratio of between 1/1 and 1/3.

18. A product obtained by performing the process as claimed in claim 7.

* * * * *